(12) United States Patent
Fujisawa et al.

(10) Patent No.: US 6,187,946 B1
(45) Date of Patent: Feb. 13, 2001

(54) JASMONIC ACID COMPOUNDS AND PROCESS FOR THE PREPARATION THEREOF

(75) Inventors: Hiroshi Fujisawa; Kazunori Watanabe, both of Kawasaki (JP)

(73) Assignee: Nippon Zeon Co., Ltd., Tokyo (JP)

( * ) Notice: Under 35 U.S.C. 154(b), the term of this patent shall be extended for 0 days.

(21) Appl. No.: 09/554,117

(22) PCT Filed: Nov. 11, 1998

(86) PCT No.: PCT/JP98/05064

§ 371 Date: May 10, 2000

§ 102(e) Date: May 10, 2000

(87) PCT Pub. No.: WO99/24388

PCT Pub. Date: May 20, 1999

(30) Foreign Application Priority Data

Nov. 12, 1997 (JP) .................................................. 9-327141

(51) Int. Cl.⁷ .................................................. C07C 69/74
(52) U.S. Cl. .................................................. 560/122
(58) Field of Search .............................................. 560/122

(56) References Cited

U.S. PATENT DOCUMENTS 5,776,860 * 7/1998 Kamuro et al. .

FOREIGN PATENT DOCUMENTS 241 821 A3   8/1987 (DE) .
2-11512      1/1990 (JP) .

OTHER PUBLICATIONS

Meyers et al, "Dihydro–1,3–oxazines. XVI. A General Synthesis of 2–Alkylcyclopentenones and a Method for Adding CH2CO2Me to Electrophilic Olefins. Application to the Synthesis of Methyl Jasmonate" in J.Org.Chem. 1973, 38, 175–176.*

* cited by examiner

*Primary Examiner*—Paul J. Killos
*Assistant Examiner*—D Khare
(74) *Attorney, Agent, or Firm*—Armstrong, Westerman, Hattori, McLeland & Naughton

(57) ABSTRACT

There are provided novel jasmonic acid compounds of the following general formula (1)

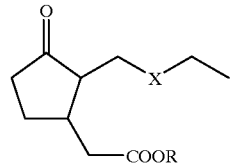

wherein R is a group selected from the group consisting of an alkenyl group of 3 to 6 carbon atoms, an alkynyl group of 3 to 6 carbon atoms, and a hydroxyalkyl group of 2 or 3 carbon atoms, and X is $CH_2$—$CH_2$ or CH=CH. These novel jasmonic acid compounds are prepared by an ester exchange reaction between a corresponding jasmonic acid methyl ester and an alcohol.

2 Claims, No Drawings

JASMONIC ACID COMPOUNDS AND PROCESS FOR THE PREPARATION THEREOF

TECHNICAL FIELD

This invention relates to novel jasmonic acid compounds and a process for preparing the same.

BACKGROUND ART

The jasmonic acid compounds which have been known prior to the filing of the present application are limited to the alkyl esters and amides of jasmonic acid and dihydrojasmonic acid, and it has been desired to develop other jasmonic acid compounds.

Accordingly, an object of the present invention is to provide novel jasmonic acid compounds and a process for preparing the same.

DISCLOSURE OF THE INVENTION

According to the present invention, there is provided a jasmonic acid compound of the following general formula (1)

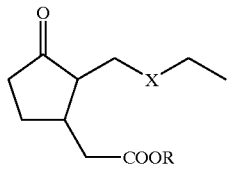
(I)

wherein R is a group selected from the group consisting of an alkenyl group of 3 to 6 carbon atoms, an alkynyl group of 3 to 6 carbon atoms, and a hydroxyalkyl group of 2 or 3 carbon atoms, and X is $CH_2$—$CH_2$ or CH=CH.

According to the present invention, there is also provided process for preparing a jasmonic acid compound of the following general formula (1)

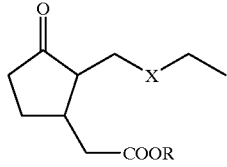
(I)

wherein R is a group selected from the group consisting of an alkenyl group of 3 to 6 carbon atoms, an alkynyl group of 3 to 6 carbon atoms, and a hydroxyalkyl group of 2 or 3 carbon atoms, and X is $CH_2$—$CH_2$ or CH=CH, which comprises effecting an ester exchange reaction by allowing an alcohol of the following general formula (3)

R—OH     (3)

wherein R is a group selected from the group consisting of an alkenyl group of 3 to 6 carbon atoms, an alkynyl group of 3 to 6 carbon atoms, and a hydroxyalkyl group of 2 or 3 carbon atoms, to act on a jasmonic acid methyl ester of the following general formula (2)

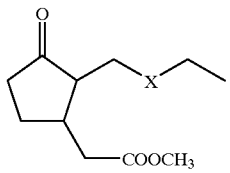
(2)

wherein X is $CH_2$—$CH_2$ or CH=CH.

In the above-described ester exchange reaction of a jasmonic acid methyl ester with an alcohol, the alcohol is usually used in an amount of 1 to 6 moles, preferably 3 to 4 moles, per mole of the jasmonic acid methyl ester.

As to the catalyst for the ester exchange reaction, any catalyst that are commonly used for ester exchange reactions may be used without limitation Usable catalysts include, for example, basic catalysts such as hydroxides and alkoxides of alkali metals and alkaline earth metals; protic acids such as sulfuric acid and p-toluenesulfonic acid; acidic ion-exchange resins; and metallic catalysts such as titanium alkoxides, aluminum alkoxides, tin compounds and lead compounds. These catalysts may be used alone or in admixture of two or more. These catalysts are usually used in an amount of about 0.05 to 20% by weight based on the weight of the alcohol.

It is not strictly necessary to use a solvent in the ester exchange reaction. Where a solvent is used, no particular limitation is placed on the type of the solvent, provided that it does not hinder the reaction. Among others, hydrocarbon solvents are preferred. Examples thereof include aromatic hydrocarbons such as benzene, toluene and xylene; and aliphatic hydrocarbons such as hexane and cyclohexane. These solvents may be used alone or in admixture of two or more. These solvents are usually used in an amount of 0 to 1,000% by weight, preferably 0 to 500% by weight and more preferably 0 to 300% by weight, based on the combined weight of the jasmonic acid methyl ester and the alcohol.

The reaction temperature for the ester exchange may usually range from room temperature to 300° C., and the pressure therefor may be either atmospheric pressure or reduced pressure.

Although the reaction is preferably carried out in an inert atmosphere, the present invention is not limited thereto. In order to promote the reaction, the methanol formed during the reaction is preferably removed by distillation. Where methanol forms an azeotrope with the solvent used, it is favorable for the promotion of the reaction to distill off the methanol from the system as an azeotrope with the solvent. Employing the above-described conditions, the reaction may usually be completed in a period of time ranging from about 30 minutes to about 20 hours. After completion of the reaction, the reaction mixture is cooled and the catalyst is removed by a suitable means such as neutralization with an aqueous alkaline solution (e.g., a solution of sodium hydroxide, sodium hydrogen carbonate or sodium carbonate), filtration, washing or acid hydrolysis. Then, the reaction mixture from which the catalyst has been removed is washed with water and optionally with a saturated aqueous solution of sodium chloride or the like. After the aqueous layer is separated, the organic layer is dried over magnesium sulfate, sodium sulfate, molecular sieve or the like, and then distilled to remove any residual solvent and any residual starting compounds. Thus, the desired jasmonic acid ester compound can be obtained. Each of the aforesaid operations may be suitably omitted, and the order of these operations may be suitably changed as required. The ester thus obtained may further be purified by distillation under reduced pressure or atmospheric pressure, chromatography or the like.

Examples of the aforesaid alcohol include methyl alcohol, ethyl alcohol, propyl alcohol, butyl alcohol, amyl alcohol, hexyl alcohol, 2-methylbutyl alcohol, allyl alcohol, cis-2-penten-1-ol, trans-2-hexen-1-ol, 3-buten-1-ol, 4-methyl-3-penten-1-ol, cis-3-hexen-1-ol, propargyl alcohol, 2-pentyn-1-ol, 3-butyn-1-ol, 3-hexyn-1-ol, ethylene glycol and propylene glycol.

Industrial Applicability

The jasmonic acid compounds of the present invention have the ability to induce the germination of parasitic plants (in particular, parasitic weeds). There is a tendency for parasitic plants to be germinated only by some components emanating from host plants. However, prior to the planting of host plants, the germination of parasitic plants can be induced by the application of a compound in accordance with the present invention. Thus, the germinated parasitic plants are made to wither before attaching themselves to hosts (i.e., the so-called suicidal germination can be induced). Accordingly, the compounds of the present invention are useful as germination inducing agents for parasitic plants.

BEST MODE FOR CARRYING OUT THE INVENTION

The present invention is further illustrated by the following examples. However, these examples are not to be construed to limit the scope of the invention. The resulting compounds were identified by proton NMR spectroscopy, IR spectroscopy and mass spectrometry.

EXAMPLE 1

Synthesis of allyl dihydrojasmonate of the following formula (by ester exchange with allyl alcohol).

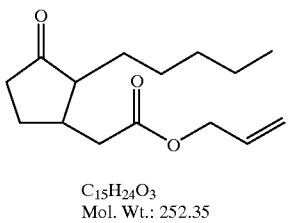

(A)

$C_{15}H_{24}O_3$
Mol. Wt.: 252.35

A 200 ml four-neck reactor fitted with a distillation column was charged with 67.8 g of methyl dihydrojasmonate, 69.7 g of allyl alcohol, and 1.2 g of a 28% methanolic solution of sodium methylate. This mixture was reacted at a temperature of 110° C. under atmospheric pressure for 3.5 hours, during which the methanol formed by the reaction was withdrawn from the top of the distillation column.

After completion of the reaction, the allyl alcohol was distilled off, and the reaction mixture was washed successively with dilute hydrochloric acid, a saturated aqueous solution of sodium hydrogen carbonate, water and a saturated aqueous solution of sodium chloride. The organic layer was dried over anhydrous magnesium sulfate, filtered, and vacuum-distilled at 0.4 mmHg to obtain a 74% yield of allyl dihydrojasmonate having a boiling point of 133–134° C. (98% pure as analyzed by gas chromatography).

Spectral data $^1$H-NMR (500 MHz, CDCl$_3$/TMS) δ (ppm): 0.86 (t, 3 H), 1.24–2.82 (16 H), 4.60 (d, 2 H), 5.23 (d, 1 H), 5.33 (d, 1 H), 5.89 (m, 1 H)

IR (Neat, capillary, cm$^{-1}$): 3087, 2958, 2933, 2861, 1744, 1733, 1650, 1461, 1410, 1382, 1333, 1241, 1171, 1090, 990, 932, 814, 724

MASS (EI, 70 eV): 41 (46), 55 (26), 69 (11), 77 (3), 83 (26), 95 (10), 109 (5), 123 (6), 133 (2), 141 (100), 153 (24), 165 (2), 182 (16), 195 (3), 211 (14), 252 (4)

EXAMPLE 2

Synthesis of cis-2-pentenyl dihydrojasmonate of the following formula (by ester exchange with cis-2-penten-1-ol).

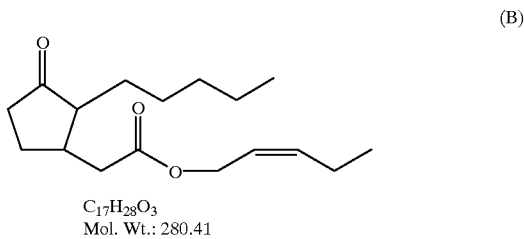

(B)

$C_{17}H_{28}O_3$
Mol. Wt.: 280.41

In substantially the same manner as in Example 1, a mixture composed of 52.5 g of methyl dihydrojasmonate, 80.7 g of cis-2-penten-1-ol, and 1.0 g of a 28% methanolic solution of sodium methylate was reacted at a temperature of 140° C. under reduced pressure (350 mmHg) for 5 hours. The reaction mixture was treated in the same manner as in Example 1, and vacuum-distilled at 0.15 mmHg to obtain a 70% yield of cis-2-pentenyl dihydrojasmonate having a boiling point of 138–141° C. (98% pure as analyzed by gas chromatography).

Spectral data $^1$H-NMR (500 MHz, CDCl$_3$/TMS) δ (ppm): 0.89 (t, 3 H), 1.00 (t, 3 H), 1.24–2.85 (18 H), 4.67 (d, 2 H), 5.51 (m, 1 H), 5.70 (m, 1 H)

IR (Neat, capillary, cm$^{-1}$): 2962, 2935, 2861, 2875, 1737, 1461, 1410, 1380, 1167, 973

MASS (EI, 70 eV): 41 (38), 55 (23), 69 (28), 83 (30), 95 (9), 109 (5), 123 (5), 133 (5), 141 (100), 153 (15), 165 (1), 195 (1), 211 (14), 280 (1)

EXAMPLE 3

Synthesis of trans-2-hexenyl dihydrojasmonate (by ester exchange with trans-2-hexen-1-ol).

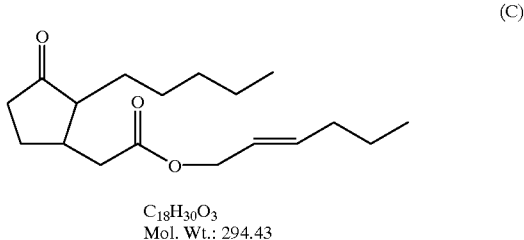

(C)

$C_{18}H_{30}O_3$
Mol. Wt.: 294.43

In substantially the same manner as in Example 1, a mixture composed of 56.9 g of methyl dihydrojasmonate, 100.0 g of trans-2-hexen-1-ol, and 1.2 g of a 28% methanolic solution of sodium methylate was reacted at a temperature of 130° C. under reduced pressure (250 mmHg) for 3 hours. The reaction mixture was treated in the same manner as in Example 1, and vacuum-distilled at 0.15 mmHg to obtain an 80% yield of trans-2-hexenyl dihydrojasmonate having a boiling point of 150–151° C. (98% pure as analyzed by gas chromatography).

Spectral data $^1$H-NMR (500 MHz, CDCl$_3$/TMS) δ (ppm): 0.86 (t, 3 H), 0.91 (t, 3 H), 1.22–2.84 (20 H), 4.57 (d, 2 H), 5.61 (m, 1 H), 5.81 (m, 1 H)

IR (Neat, capillary, cm$^{-1}$): 2960, 2933, 2875, 2863, 1737, 1461, 1410, 1382, 1335, 1264, 1252, 1167, 973

MASS (EI, 70 eV): 41 (34), 55 (46), 67 (16), 83 (29), 95 (8), 109 (5), 123 (5), 133 (4), 141 (100), 153 (39), 165 (1), 195 (1), 211 (11), 224 (2), 294 (1)

EXAMPLE 4

Synthesis of 3-butenyl dihydrojasmonate of the following formula (by ester exchange with 3-buten-1-ol).

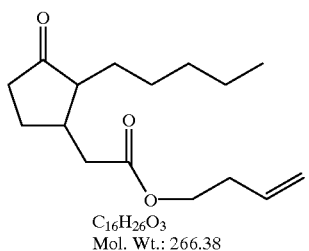

(D)

C$_{16}$H$_{26}$O$_3$
Mol. Wt.: 266.38

In substantially the same manner as in Example 1, a mixture composed of 56.5 g of methyl dihydrojasmonate, 72.1 g of 3-buten-1-ol, and 1.2 g of a 28% methanolic solution of sodium methylate was reacted at a temperature of 100° C. under reduced pressure (500 mmHg) for 9 hours. The reaction mixture was treated in the same manner as in Example 1, and vacuum-distilled at 0.9 mmHg to obtain a 73% yield of 3-butenyl dihydrojasmonate having a boiling point of 164–165° C. (95% pure as analyzed by gas chromatography).

Spectral data $^1$H-NMR (500 MHz, CDCl$_3$/TMS) δ (ppm): 0.88 (t, 3 H), 1.21–2.84 (18 H), 4.20 (t, 2 H), 5.12 (d, 1 H), 5.16 (d, 1 H), 5.81 (m, 1 H)

IR (Neat, capillary, cm$^{-1}$): 3462, 3081, 2960, 2933, 2861, 1742, 1644, 1461, 1410, 1335, 1250, 1171, 990, 919, 812, 724

MASS (EI, 70 eV): 41 (42), 55 (100), 67 (20), 83 (92), 96 (29), 107 (4), 114 (11), 123 (7), 133 (4), 141 (38), 153 (88), 160 (1), 168 (8), 181 (7), 196 (25), 211 (4), 266 (8)

EXAMPLE 5

Synthesis of 4-methyl-3-pentenyl dihydrojasmonate of the following formula (by ester exchange with 4-methyl-3-penten-1-ol).

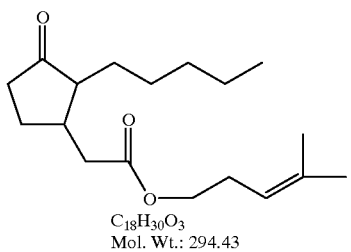

(E)

C$_{18}$H$_{30}$O$_3$
Mol. Wt.: 294.43

In substantially the same manner as in Example 1, a mixture composed of 6.0 g of methyl dihydrojasmonate, 10.1 g of 4-methyl-3-penten-1-ol, and 0.3 g of a 28% methanolic solution of sodium methylate was reacted at a temperature of 130° C. under reduced pressure (200 mmHg) for 3 hours. The reaction mixture was treated in the same manner as in Example 1, and vacuum-distilled at 0.2 mmHg to obtain a 75% yield of 4-methyl-3-pentenyl dihydrojasmonate having a boiling point of 146–148° C. (95% pure as analyzed by gas chromatography).

Spectral data $^1$H-NMR (500 MHz, CDCl$_3$/TMS) δ (ppm): 0.89 (t, 3 H), 1.22–2.84 (18 H), 1.64 (s, 3 H), 1.72 (s, 3 H), 4.09 (t, 2 H), 5.14 (t, 1 H)

IR (Neat, capillary, cm$^{-1}$): 3460, 2960, 2933, 2861, 2732, 1744, 1459, 1410, 1380, 1335, 1252, 1171, 1121, 1071, 1003, 830, 760, 726

MASS (EI, 70 eV): 41 (22), 55 (28), 67 (28), 82 (100), 97 (3), 109 (1), 123 (1), 133 (1), 141 (5), 153 (7), 165 (1), 177 (1), 195 (2), 213 (3), 224 (1), 294 (1)

EXAMPLE 6

Synthesis of cis-3-hexenyl dihydrojasmonate of the following formula (by ester exchange with cis-3-hexen-1-ol).

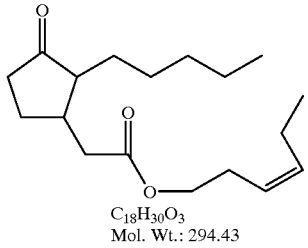

(F)

C$_{18}$H$_{30}$O$_3$
Mol. Wt.: 294.43

In substantially the same manner as in Example 1, a mixture composed of 67.8 g of methyl dihydrojasmonate, 120.4 g of cis-3-hexen-1-ol, and 1.2 g of a 28% methanolic solution of sodium methylate was reacted at a temperature of 130° C. under reduced pressure (200 mmHg) for 10 hours. The reaction mixture was treated in the same manner as in Example 1, and vacuum-distilled at 0.06 mmHg to obtain a 70% yield of cis-3-hexenyl dihydrojasmonate having a boiling point of 135–136° C. (98% pure as analyzed by gas chromatography).

Spectral data $^1$H-NMR (500 MHz, CDCl$_3$/TMS) δ (ppm): 0.88 (t, 3 H), 0.98 (t, 3 H), 1.26–2.84 (20 H), 4.12 (t, 2 H), 5.36 (m, 1 H), 5.55 (m, 1 H)

IR (Neat, capillary, cm$^{-1}$): 3012, 2962, 2933, 2861, 2873, 1740, 1463, 1410, 1389, 1335, 1250, 1169, 1136, 1071, 1003

MASS (EI, 70 eV): 41 (36), 55 (56), 67 (52), 82 (100), 96 (8), 109 (4), 123 (3), 133 (2), 141 (36), 153 (43), 165 (2), 177 (1), 195 (4), 211 (4), 294 (2)

EXAMPLE 7

Synthesis of propargyl dihydrojasmonate of the following formula (by ester exchange with propargyl alcohol).

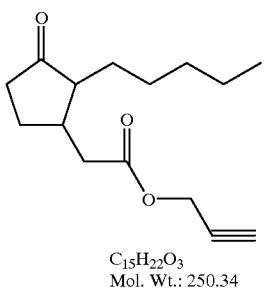

(G)

C$_{15}$H$_{22}$O$_3$
Mol. Wt.: 250.34

In substantially the same manner as in Example 1, a mixture composed of 67.8 g of methyl dihydrojasmonate, 67.3 g of propargyl alcohol, and 1.2 g of a 28% methanolic solution of sodium methylate was reacted at a temperature of 110° C. under reduced pressure (400 mmHg) for 7 hours. The reaction mixture was treated in the same manner as in Example 1, and vacuum-distilled at 0.3 mmHg to obtain a 70% yield of propargyl dihydrojasmonate having a boiling point of 135–137° C. (97% pure as analyzed by gas chromatography).

Spectral data $^1$H-NMR (500 MHz, CDCl$_3$/TMS) δ (ppm): 0.88 (t, 3 H), 1.05–2.51 (16 H), 2.21 (t, 1 H), 4.73 (d, 2 H)

IR (Neat, capillary, cm$^{-1}$): 3274, 2958, 2933, 2861, 2310, 2242, 1737, 1461, 1410, 1380, 1322, 1243, 1164, 1084, 1023, 976, 953, 782, 726

MASS (EI, 70 eV): 39 (27), 41 (21), 45 (1), 55 (26), 67 (13), 77 (4), 83 (46), 95 (13), 109 (7), 123 (4), 134 (2), 141 (100), 153 (25), 165 (2), 180 (6), 194 (2), 211 (7), 250 (2)

EXAMPLE 8

Synthesis of 2-pentynyl dihydrojasmonate of the following formula (by ester exchange with 2-pentyn-1-ol).

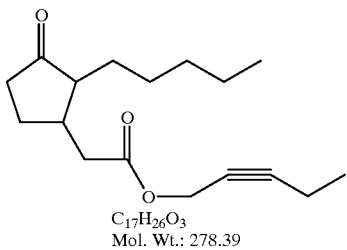

(H)

C$_{17}$H$_{26}$O$_3$
Mol. Wt.: 278.39

In substantially the same manner as in Example 1, a mixture composed of 56.5 g of methyl dihydrojasmonate, 85.3 g of 2-pentyn-1-ol, and 1.0 g of a 28% methanolic solution of sodium methylate was reacted at a temperature of 130° C. under reduced pressure (250 mmHg) for 6 hours. The reaction mixture was treated in the same manner as in Example 1, and vacuum-distilled at 0.15 mmHg to obtain a 70% yield of 2-pentynyl dihydrojasmonate having a boiling point of 139–141° C. (95% pure as analyzed by gas chromatography).

Spectral data $^1$H-NMR (500 MHz, CDCl$_3$/TMS) δ (ppm): 0.88 (t, 3 H), 1.15 (t, 3 H), 1.22–2.85 (18 H), 4.72 (d, 2 H)

IR (Neat, capillary, cm$^{-1}$): 3462, 2958, 2933, 2861, 2310, 2242, 1737, 1461, 1410, 1380, 1322, 1243, 1164, 1084, 1023, 976, 953, 782, 726

MASS (EI, 70 eV): 41 (29), 55 (20), 67 (17), 83 (20), 95 (8), 109 (5), 123 (6), 133 (3), 141 (100), 153 (17), 165 (1), 179 (1), 193 (4), 211 (19), 278 (2)

EXAMPLE 9

Synthesis of 3-butynyl dihydrojasmonate of the following formula (by ester exchange with 3-butyn-1-ol).

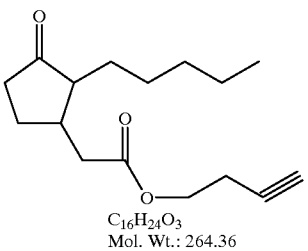

(I)

C$_{16}$H$_{24}$O$_3$
Mol. Wt.: 264.36

In substantially the same manner as in Example 1, a mixture composed of 67.8 g of methyl dihydrojasmonate, 84.2 g of 3-butyn-1-ol, and 1.2 g of a 28% methanolic solution of sodium methylate was reacted at a temperature of 120° C. under reduced pressure (350 mmHg) for 10 hours. The reaction mixture was treated in the same manner as in Example 1, and vacuum-distilled at 0.06 mmHg to obtain a 70% yield of 3-butynyl dihydrojasmonate having a boiling point of 148–149° C. (95% pure as analyzed by gas chromatography).

Spectral data $^1$H-NMR (500 MHz, CDCl$_3$/TMS) δ (ppm): 0.88 (t, 3 H), 1.24–2.85 (18 H), 2.03 (t, 1 H), 4.24 (t, 2 H)

IR (Neat, capillary, cm$^{-1}$): 3284, 2958, 2933, 2861, 1744, 1459, 1410, 1391, 1335, 1248, 1169, 1084, 1036, 1005, 645

MASS (EI, 70 eV): 41 (38), 55 (43), 69 (21), 83 (100), 96 (24), 105 (4), 109 (11), 113 (30), 121 (14), 135 (41), 141 (11), 153 (59), 165 (8), 179 (5), 195 (11), 207 (4), 225 (4), 239 (3), 264 (2)

EXAMPLE 10

Synthesis of 3-hexynyl dihydrojasmonate of the following formula (by ester exchange with 3-hexyn-1-ol).

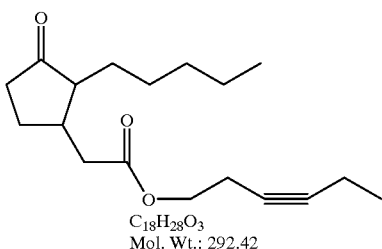

C₁₈H₂₈O₃
Mol. Wt.: 292.42

(J)

In substantially the same manner as in Example 1, a mixture composed of 56.5 g of methyl dihydrojasmonate, 98.2 g of 3-hexyn-1-ol, and 1.0 g of a 28% methanolic solution of sodium methylate was reacted at a temperature of 130° C. under reduced pressure (200 mmHg) for 5 hours The reaction mixture was treated in the same manner as in Example 1, and vacuum-distilled at 0.15 mmHg to obtain a 70% yield of 3-hexynyl dihydrojasmonate having a boiling point of 153–155° C. (98% pure as analyzed by gas chromatography).

Spectral data $^1$H-NMR (500 MHz, CDCl$_3$/TMS) δ (ppm): 0.88 (t, 3 H), 1.11 (t, 3 H), 1.22–2.85 (20 H), 4.20 (t, 2 H)

IR (Neat, capillary, cm$^{-1}$): 2960, 2933, 2861, 1744, 1461, 1410, 1391, 1337, 1250, 1169, 1084, 1073, 1019, 814, 726

MASS (EI, 70 eV): 41 (21), 55 (57), 67 (28), 79 (100), 83 (93), 96 (30), 109 (12), 125 (20), 133 (6), 135 (17), 141 (38), 153 (70), 163 (22), 177 (5), 193 (9), 213 (9), 222 (5), 239 (1), 292 (3)

EXAMPLE 11

Synthesis of 2-hydroxyethyl dihydrojasmonate of the following formula (by ester exchange with ethylene glycol).

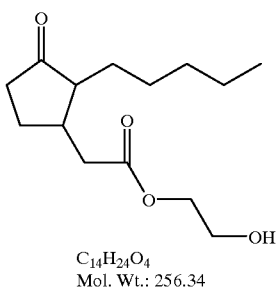

C₁₄H₂₄O₄
Mol. Wt.: 256.34

(K)

In substantially the same manner as in Example 1, a mixture composed of 56.8 g of methyl dihydrojasmonate, 76.1 g of ethylene glycol, and 1.0 g of a 28% methanolic solution of sodium methylate was reacted at a temperature of 140° C. under reduced pressure (100 mmHg) for 4 hours. The reaction mixture was treated in the same manner as in Example 1, and vacuum-distilled at 0.1 mmHg to obtain a 15% yield of 2-hydroxyethyl dihydrojasmonate having a boiling point of 157–160° C. (98% pure as analyzed by gas chromatography).

Spectral data $^1$H-NMR (500 MHz, CDCl$_3$/TMS) δ (ppm): 0.88 (t, 3 H), 1.24–2.84 (17 H), 3.83 (t, 2 H), 4.21 (t, 2 H)

IR (Neat, capillary, cm$^{-1}$): 3458, 2958, 2933, 2861, 1739, 1461, 1409, 1382, 1335, 1254, 1171, 1082, 1032, 951, 886, 724

MASS (EI, 70 eV): 41 (21), 55 (26), 67 (15), 79 (8), 83 (100), 96 (23), 104 (32), 110 (8), 117 (1), 123 (4), 135 (2), 141 (12), 153 (54), 163 (2), 177 (1), 186 (17), 193 (6), 211 (1), 225 (1), 239 (1), 256 (2)

EXAMPLE 12

Synthesis of 2-hydroxypropyl dihydrojasmonate of the following formula (by ester exchange with 2-propylene glycol).

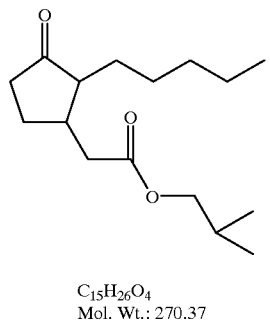

C₁₅H₂₆O₄
Mol. Wt.: 270.37

(L)

In substantially the same manner as in Example 1, a mixture composed of 56.8 g of methyl dihydrojasmonate, 76.1 g of 1,2-propylene glycol, and 1.0 g of a 28% methanolic solution of sodium methylate was reacted at a temperature of 140° C. under reduced pressure (100 mmHg) for 4 hours. The reaction mixture was treated in the same manner as in Example 1, and vacuum-distilled at 0.1 mmHg to obtain a 45% yield of a mixture of 2-hydroxypropyl dihydrojasmonate and 1-methyl-2-hydroxyethyl dihydrojasmonate having a boiling point of 156–159° C. (98% pure as analyzed by gas chromatography).

Spectral data $^1$H-NMR (500 MHz, CDCl$_3$/TMS) δ (ppm): 0.88 (t, 3 H), 1.22–2.80 (20 H), 3.64–4.12 (3 H)

IR (Neat, capillary, cm$^{-1}$): 3462, 2958, 2933, 2861, 1737, 1461, 1409, 1380, 1335, 1264, 1171, 1057, 994, 951, 849

MASS (EI, 70 eV): 41 (33), 55 (38), 67 (19), 83 (93), 96 (48), 109 (10), 118 (50), 125 (6), 133 (2), 141 (27), 153 (100), 165 (3), 177 (2), 195 (7), 200 (12), 211 (3), 226 (1), 270 (2)

EXAMPLE 13

Synthesis of allyl jasmonate of the following formula (by ester exchange with allyl alcohol).

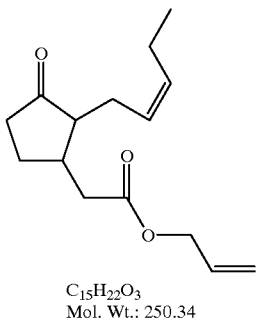

C₁₅H₂₂O₃
Mol. Wt.: 250.34

(M)

A 200 ml four-neck reactor fitted with a distillation column was charged with 50.0 g of methyl jasmonate, 51.8 g of allyl alcohol, and 1.0 g of a 28% methanolic solution of sodium methylate. This mixture was reacted at a temperature of 110° C. under atmospheric pressure for 6 hours, during which the methanol formed by the reaction was withdrawn from the top of the distillation column.

After completion of the reaction, the allyl alcohol was distilled off, and the reaction mixture was washed successively with dilute hydrochloric acid, a saturated aqueous solution of sodium hydrogen carbonate, water and a saturated aqueous solution of sodium chloride. The organic layer was dried over anhydrous magnesium sulfate, filtered, and vacuum-distilled at 0.4 mmHg to obtain a 70% yield of allyl jasmonate having a boiling point of 132–134° C. (97% pure as analyzed by gas chromatography).

Spectral data $^1$H-NMR (400 MHz, CDCl$_3$/TMS) δ (ppm): 0.96 (t, 3 H), 1.51 (m, 1 H), 1.8–2.4 (10 H), 2.72 (q, 1 H), 4.61 (m, 2 H), 5.2–5.4 (3 H), 5.47 (q, 1 H), 5.96 (m, 1 H)

IR (Neat, KBr, cm$^{-1}$): 3461, 3086, 3009, 2963, 2934, 2876, 1738, 1649, 1460, 1410, 1383, 1333, 1231, 1163, 990, 932, 737

MASS (EI, 70 eV): 39 (45), 41 (100), 55 (46), 67 (37), 79 (37), 83 (34), 93 (29), 95 (29), 107 (31), 121 (27), 131 (23), 141 (75), 149 (30), 151 (38), 163 (10), 182 (11), 191 (15), 209 (14), 232 (2), 250 (33)

EXAMPLE 14

Synthesis of propargyl jasmonate of the following formula (by ester exchange with propargyl alcohol).

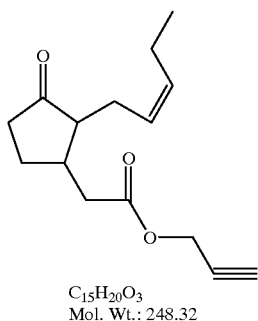

(N)

C$_{15}$H$_{20}$O$_3$
Mol. Wt.: 248.32

In substantially the same manner as in Example 13, a mixture composed of 50.2 g of methyl jasmonate, 51.0 g of propargyl alcohol, and 1.0 g of a 28% methanolic solution of sodium methylate was reacted at a temperature of 125° C. under atmospheric pressure for 15 hours. The reaction mixture was treated in the same manner as in Example 13, and vacuum-distilled at 0.6 mmHg to obtain a 56% yield of propargyl jasmonate having a boiling point of 163–164° C. (97% pure as analyzed by gas chromatography).

Spectral data $^1$H-NMR (400 MHz, CDCl$_3$/TMS) δ (ppm): 0.95 (t, 3 H), 1.51 (m, 1 H), 1.8–3.0 (12 H), 4.69 (d, 2 H), 5.27 (q, 1 H), 5.44 (q, 1 H)

IR (Neat, KBr, cm$^{-1}$): 3461, 3287, 3009, 2965, 2936, 2876, 2130, 1740, 1437, 1408, 1385, 1333, 1231, 1159, 1024, 995, 937, 868, 824, 797, 677, 527

MASS (EI, 70 eV): 39 (100), 41 (72), 55 (60), 67 (53), 79 (53), 83 (68), 95 (48), 107 (27), 109 (33), 121 (24), 133 (21), 135 (26), 141 (95), 151 (77), 163 (10), 180 (10), 191 (13), 201 (6), 209 (10), 219 (5), 230 (2), 248 (24)

EXAMPLE 15

Synthesis of 3-butenyl jasmonate of the following formula (by ester exchange with 3-buten-1-ol).

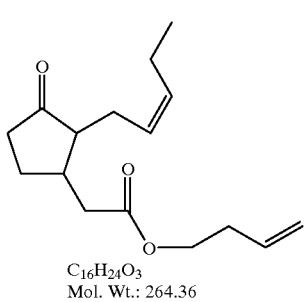

(O)

C$_{16}$H$_{24}$O$_3$
Mol. Wt.: 264.36

In substantially the same manner as in Example 13, a mixture composed of 56.5 g of methyl jasmonate, 30.0 g of 3-buten-1-ol, and 1.0 g of a 28% methanolic solution of sodium methylate was reacted at a temperature of 155° C. under atmospheric pressure for 5 hours. The reaction mixture was treated in the same manner as in Example 13, and vacuum-distilled at 0.9 mmHg to obtain a 57% yield of 3-butenyl jasmonate having a boiling point of 142° C. (97% pure as analyzed by gas chromatography).

Spectral data $^1$H-NMR (400 MHz, CDCl$_3$/TMS) δ (ppm): 0.95 (t, 3 H), 1.50 (m, 1 H), 1.80–2.60 (12 H), 2.71 (m, 1 H), 4.15 (t, 2 H), 5.10 (2 H), 5.25 (q, 1 H), 5.44 (q, 1 H), 5.78 (m, 1 H)

IR (Neat, KBr, cm$^{-1}$): 3461, 3079, 2963, 2934, 1738, 1644, 1460, 1435, 1408, 1387, 1335, 1233, 1165, 990, 918, 669

MASS (EI, 70 eV): 39 (38), 41 (54), 55 (100), 67 (35), 79 (32), 83 (53), 95 (31), 109 (24), 121 (20), 133 (17), 135 (21), 141 (19), 151 (61), 163 (8), 193 (26), 217 (7), 246 (3), 264 (33)

EXAMPLE 16

Synthesis of 3-butynyl jasmonate of the following formula (by ester exchange with 3-butyn-1-ol).

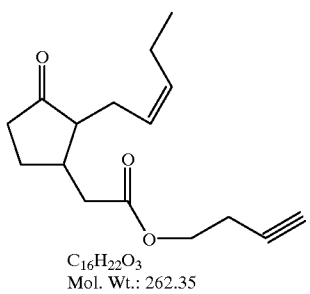

(P)

C$_{16}$H$_{22}$O$_3$
Mol. Wt.: 262.35

In substantially the same manner as in Example 13, a mixture composed of 30.0 g of methyl jasmonate, 51.7 g of 3-butyn-1-ol, and 1.0 g of a 28% methanolic solution of sodium methylate was reacted at a temperature of 150° C. under atmospheric pressure for 7 hours. The reaction mixture was treated in the same manner as in Example 13, and vacuum-distilled at 0.5 mmHg to obtain a 52% yield of 3-butynyl jasmonate having a boiling point of 138° C. (97% pure as analyzed by gas chromatography).

Spectral data $^{1}$H-NMR (400 MHz, CDCl$_3$/TMS) δ (ppm): 0.96 (t, 3 H), 1.51 (m, 1 H), 1.80–2.80 (14 H), 4.21 (t, 2 H), 5.27 (q, 1 H), 5.45 (q, 1 H)

IR (Neat, KBr, cm$^{-1}$): 3457, 3289, 3007, 2965, 2934, 2876, 2123, 1738, 1460, 1408, 1390, 1335, 1231, 1163, 1092, 1071, 1038, 1003, 820, 650, 552

MASS (EI, 70 eV): 39 (52), 41 (79), 53 (91), 55 (66), 67 (60), 79 (57), 83 (100), 95 (56), 109 (44), 121 (34), 133 (30), 135 (44), 151 (81), 163 (10), 193 (83), 205 (8), 215 (7), 233 (5), 247 (3), 262 (3)

EXAMPLE 17

Synthesis of cis-3-hexenyl jasmonate of the following formula (by ester exchange with cis-3-hexen-1-ol).

(Q)

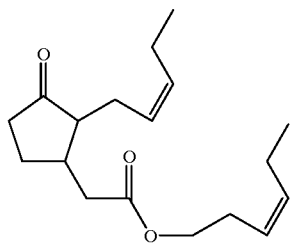

C$_{18}$H$_{28}$O$_3$
Mol. Wt.: 292.42

In substantially the same manner as in Example 13, a mixture composed of 50.0 g of methyl jasmonate, 88.0 g of cis-3-hexen-1-ol, and 1.0 g of a 28% methanolic solution of sodium methylate was reacted at a temperature of 130° C. under reduced pressure (200 mmHg) for 11 hours. The reaction mixture was treated in the same manner as in Example 13, and vacuum-distilled at 0.7 mmHg to obtain a 56% yield of cis-3-hexenyl jasmonate having a boiling point of 154–156° C. (98% pure as analyzed by gas chromatography).

Spectral data $^{-1}$H-NMR (400 MHz, CDCl$_3$/TMS) δ (ppm): 0.96 (6 H), 1.50 (m, 1 H), 1.80–2.50 (14 H), 2.69 (m, 1 H), 4.10 (t, 2 H), 5.28 (2 H), 5.48 (2 H)

IR (Neat, KBr, cm$^{-1}$): 3461, 3011, 2965, 2934, 2876, 1738, 1655, 1460, 1408, 1389, 1335, 1231, 1165, 1090, 1071, 1046, 1003, 903, 797, 729, 583

MASS (EI, 70 eV): 41 (78), 55 (100), 67 (64), 82 (42), 83 (58), 95 (20), 107 (14), 121 (14), 135 (13), 141 (29), 151 (53), 163 (9), 193 (11), 210 (17), 274 (2), 292 (15)

What is claimed is:

1. A jasmonic acid compound of the following general formula (1)

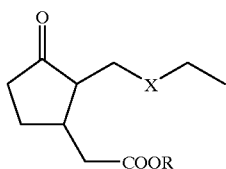

(I)

wherein R is a group selected from the group consisting of an alkenyl group of 3 to 6 carbon atoms, an alkynyl group of 3 to 6 carbon atoms, and a hydroxyalkyl group of 2 or 3 carbon atoms, and X is CH$_2$—CH$_2$ or CH=CH.

2. A process for preparing a jasmonic acid compound of the following general formula (1)

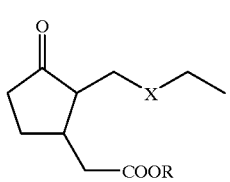

(I)

wherein R is a group selected from the group consisting of an alkenyl group of 3 to 6 carbon atoms, an alkynyl group of 3 to 6 carbon atoms, and a hydroxyalkyl group of 2 or 3 carbon atoms, and X is CH$_2$—CH$_2$ or CH=CH, which comprises effecting an ester exchange reaction by allowing an alcohol of the following general formula (3)

R—OH　　　　(3)

wherein R is a group selected from the group consisting of an alkenyl group of 3 to 6 carbon atoms, an alkynyl group of 3 to 6 carbon atoms, and a hydroxyalkyl group of 2 or 3 carbon atoms, to act on a jasmonic acid methyl ester of the following general formula (2)

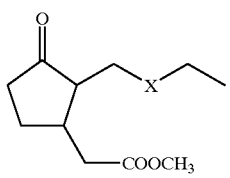

(2)

wherein X is CH$_2$—CH$_2$ or CH=CH.

* * * * *